(12) United States Patent
Shaham et al.

(10) Patent No.: US 8,037,696 B2
(45) Date of Patent: Oct. 18, 2011

(54) METHOD AND APPARATUS FOR FREEZING OR THAWING OF A BIOLOGICAL MATERIAL

(75) Inventors: Ginadi Shaham, Yavneh (IL); Udi Damari, Ganiey Tikva (IL); Benny Rousso, Rishon LeZion (IL)

(73) Assignee: Core Dynamics Limited, Hamilton (BM)

( * ) Notice: Subject to any disclaimer, the term of this patent is extended or adjusted under 35 U.S.C. 154(b) by 237 days.

(21) Appl. No.: 11/658,859

(22) PCT Filed: Aug. 14, 2005

(86) PCT No.: PCT/IL2005/000876
§ 371 (c)(1), (2), (4) Date: Aug. 1, 2007

(87) PCT Pub. No.: WO2006/016372
PCT Pub. Date: Feb. 16, 2006

(65) Prior Publication Data
US 2008/0120984 A1 May 29, 2008

Related U.S. Application Data

(60) Provisional application No. 60/600,804, filed on Aug. 12, 2004.

(51) Int. Cl.
*F25D 25/00* (2006.01)
(52) U.S. Cl. .............. 62/62; 62/63; 62/75; 62/371
(58) Field of Classification Search ............. 62/62, 63, 62/75, 371
See application file for complete search history.

(56) References Cited

U.S. PATENT DOCUMENTS

| | | | |
|---|---|---|---|
| 3,074,247 A | 1/1963 | Polk | |
| 3,347,745 A | 10/1967 | Rinfret et al. | |
| 4,018,911 A | 4/1977 | Lionetti et al. | |
| 4,117,881 A | 10/1978 | Williams et al. | |
| 4,480,682 A * | 11/1984 | Kaneta et al. | 165/206 |
| 4,620,908 A | 11/1986 | Van Duzer | |

(Continued)

FOREIGN PATENT DOCUMENTS

DE 100 56 181 C1 3/2002

(Continued)

OTHER PUBLICATIONS

Gao, et al., "Development of a Directional Solidification Device for Cell Cryopreservation", Cell Preservation Technology, vol. 1, No. 4, pp. 231-238, (2003).

(Continued)

*Primary Examiner* — Cheryl J Tyler
*Assistant Examiner* — Jonathan Koagel
(74) *Attorney, Agent, or Firm* — The Nath Law Group; Susanne M. Hopkins; Wiliam L. Klima

(57) ABSTRACT

The temperature of a biological material is changed from a first temperature to a second temperature within a time period, one of the said first or second temperature being above freezing temperature and the other being below freezing temperature, by placing the biological material in tight contact with at least one, preferably between two heat exchangers, and controlling the temperature in at least one of said heat exchangers such that a freezing temperature front propagates in said material away from at least one of the two heat exchangers.

31 Claims, 1 Drawing Sheet

U.S. PATENT DOCUMENTS

| | | | |
|---|---|---|---|
| 4,857,319 A | 8/1989 | Crowe et al. | |
| 4,874,690 A | 10/1989 | Goodrich, Jr. et al. | |
| 5,059,518 A | 10/1991 | Kortright et al. | |
| 5,071,598 A | 12/1991 | Baldeschwieler et al. | |
| 5,131,850 A | 7/1992 | Brockbank | |
| 5,364,756 A | 11/1994 | Livesey et al. | |
| 5,418,130 A | 5/1995 | Platz et al. | |
| 5,587,490 A | 12/1996 | Goodrich, Jr. et al. | |
| 5,629,145 A | 5/1997 | Meryman | |
| 5,709,992 A | 1/1998 | Rubinstein | |
| 5,827,741 A | 10/1998 | Beattie et al. | |
| 5,843,780 A | 12/1998 | Thomson | |
| 5,863,715 A | 1/1999 | Rajotte et al. | |
| 5,869,092 A | 2/1999 | Hays et al. | |
| 5,873,254 A | 2/1999 | Arav | |
| 5,897,987 A | 4/1999 | Oliver et al. | |
| 5,955,257 A | 9/1999 | Burger et al. | |
| 6,007,978 A | 12/1999 | Goodrich, Jr. et al. | |
| 6,073,540 A | 6/2000 | Garrett | |
| 6,146,890 A | 11/2000 | Danon | |
| 6,319,914 B1 | 11/2001 | Simpkins et al. | |
| 6,337,205 B1 | 1/2002 | Wisniewski | |
| 6,453,683 B1 * | 9/2002 | Wisniewski et al. | 62/75 |
| 6,482,585 B2 | 11/2002 | Dottori | |
| 6,488,033 B1 | 12/2002 | Cerundolo | |
| 6,723,497 B2 | 4/2004 | Wolkers et al. | |
| 6,740,484 B1 | 5/2004 | Khirabadi et al. | |
| 6,887,704 B2 | 5/2005 | Peled et al. | |
| 2002/0119946 A1 | 8/2002 | Gen | |
| 2002/0177116 A1 | 11/2002 | Wiggins et al. | |
| 2003/0059338 A1 | 3/2003 | Mann et al. | |
| 2003/0068416 A1 | 4/2003 | Burgess et al. | |
| 2004/0006999 A1 | 1/2004 | Brown et al. | |
| 2004/0067157 A1 | 4/2004 | MacPhee et al. | |
| 2004/0129003 A1 | 7/2004 | Voute et al. | |
| 2004/0191754 A1 | 9/2004 | Meir et al. | |
| 2004/0197310 A1 | 10/2004 | Sanberg et al. | |
| 2005/0008623 A1 | 1/2005 | Bechetoille et al. | |
| 2005/0020524 A1 | 1/2005 | Boyd | |
| 2005/0042754 A1 | 2/2005 | Miyazaki et al. | |
| 2005/0059152 A1 | 3/2005 | Tanavde et al. | |
| 2005/0095228 A1 | 5/2005 | Fraser et al. | |
| 2005/0118712 A1 | 6/2005 | Tsai et al. | |
| 2005/0142118 A1 | 6/2005 | Wernet | |
| 2006/0035383 A1 | 2/2006 | Ho et al. | |
| 2006/0057555 A1 | 3/2006 | Damari et al. | |
| 2007/0077237 A1 | 4/2007 | Damari et al. | |
| 2007/0277535 A1 | 12/2007 | Uri et al. | |
| 2008/0120984 A1 | 5/2008 | Shaham et al. | |

FOREIGN PATENT DOCUMENTS

| | | |
|---|---|---|
| EP | 0 664 080 A1 | 7/1995 |
| EP | 0 668 013 A2 | 8/1995 |
| EP | 1 057 405 A1 | 12/2000 |
| EP | 1 131 998 A1 | 9/2001 |
| EP | 1 471 140 A1 | 10/2004 |
| EP | 1 535 514 A1 | 6/2005 |
| EP | 1 627 565 A1 | 2/2006 |
| GB | 1 279 356 | 6/1972 |
| JP | 2000-189155 A | 7/2000 |
| WO | 91/06213 A1 | 5/1991 |
| WO | 91/16060 A1 | 10/1991 |
| WO | 93/00806 A1 | 1/1993 |
| WO | 97/35472 A1 | 10/1997 |
| WO | 97/39104 A1 | 10/1997 |
| WO | 98/10231 A1 | 3/1998 |
| WO | 98/46072 A1 | 10/1998 |
| WO | 99/60849 A1 | 12/1999 |
| WO | 00/29551 A2 | 5/2000 |
| WO | 01/23532 A1 | 4/2001 |
| WO | 01/45503 A2 | 6/2001 |
| WO | 01/50852 A2 | 7/2001 |
| WO | 01/87062 A2 | 11/2001 |
| WO | 02/32225 A2 | 4/2002 |
| WO | 02/076206 A2 | 10/2002 |
| WO | 03/020874 A2 | 3/2003 |
| WO | 03/056919 A2 | 7/2003 |
| WO | WO 03056919 * | 7/2003 |
| WO | 03/099040 A1 | 12/2003 |
| WO | 2004/009138 A2 | 1/2004 |
| WO | 2004/055456 A1 | 7/2004 |
| WO | WO 2004055456 A1 * | 7/2004 |
| WO | 2004/098285 A2 | 11/2004 |
| WO | 2005/032251 A1 | 4/2005 |
| WO | 2005/056755 A2 | 6/2005 |
| WO | 2005/072523 A2 | 8/2005 |
| WO | 2005/072790 A1 | 8/2005 |
| WO | 2006/016372 A1 | 2/2006 |
| WO | 2008/032314 A2 | 3/2008 |

OTHER PUBLICATIONS

Ahlenstiel, et al., "Bioflavonoids attenuate renal proximal tubular cell injury during cold preservation in Euro-Collins and University of Wisconsin solutions", Kidney International, vol. 63, pp. 554-563, (2003). XP-002337114.

Chen, et al., "Beneficial Effect of Intracellular Trehalose on the Membrane Integrity of Dried Mammalian Cells", Cryobiology, vol. 43, pp. 168-181, (2001).

Chow, et al., "Phase I Pharmacokinetic Study of Tea Polyphenols following Single-dose Administration of Epigallocatechin Gallate and Polyphenon E", Cancer Epidemiology, Biomarkers & Prevention, vol. 10, pp. 53-58, (2001).

Crowe, et al., "Stabilization of membranes in human platelets freeze-dried with trehalose", Chemistry and Physics of Lipids, vol. 122, pp. 41-52, (2003).

Csönge, et al., "Banking of osteochondral allografts, Part II. Preservation of Chondrocyte Viability During Long-Term Storage", Cell and Tissue Banking, vol. 3, pp. 161-168, (2002). XP-002313332.

De Korte, et al., "Quality Determinants of Erythrocyte Destined for Transfusion", Cellular and Molecular Biology, vol. 50, No. 2, pp. 187-195, (2004).

Fujiki, et al., "Mechanistic Findings of Green Tea as Cancer Preventive for Humans", P.S.E.B.M., vol. 220, pp. 225-228, (1999).

Galati, et al., "Prooxidant activity and cellular effects of the phenoxyl radicals of dietary flavonoids and other polyphenolics", Toxicology, vol. 177, pp. 91-104, (2002).

Goodrich, et al., "Preservation of metabolic activity in lyophilized human erythrocytes", Proc. Natl. Acad. Sci. USA, vol. 89, pp. 967-971, (1992).

Grinberg, et al., "Protective Effects of Tea Polyphenols against Oxidative Damage to Red Blood Cells", Biochemical Pharmacology, vol. 54, pp. 973-978, (1997).

Han, et al., "Protection of osteoblastic cells from freeze/thaw cycle-induced oxidative stress by green tea polyphenol", Biotechnology Letters, vol. 27, pp. 655-660, (2005).

Higgs, et al., "Cartilage Regeneration and Repair, Where Are We?" Proceedings of the International Cartilage Repair Society's Second Symposium, (1998).

Jomha, et al., "Cryopreservation of intact human articular cartilage", Journal of Orthopaedic Research, vol. 20, pp. 1253-1255, (2002).

Kumazawa, et al., "Direct Evidence of Interaction of a Green Tea Polyphenol, Epigallocatechin Gallate, with Lipid Bilayers by Solid-state Nuclear Magnetic Resonance", Biosci. Biotechnol. Biochem., vol. 68, No. 8, pp. 1743-1747, (2004).

Kusakabe, et al., "Maintenance of genetic integrity in frozen and freeze-dried mouse spermatozoa", Proc Natl Acad Sci U S A, vol. 98, No. 24, pp. 13501-13506, (2001).

Kushibe, et al., "Tracheal Allotransplantation Mantaining Cartilage Viability with Long-Term Cryopreserved Allografts", Ann Thorac Surg, vol. 71, pp. 1666-1669, (2001).

Laprade, et al., "Refrigerated Osteoarticular Allografts to Treat Articular Cartilage Defects of the Femoral Condyles. A Prospective Outcomes Study", J Bone Joint Surg Am, vol. 91, pp. 805-811, (2009).

Lelkens, et al., "Stability after thawing of RBCs frozen with the high- and low-glycerol method", Transfusion, vol. 43, pp. 157-164, (2003).

López, et al., "Determination of Viability of Human Cartilage Allografts by a Rapid and Quantitative Method Not Requiring Cartilage Digestion", Cell Transplantation, vol. 17, pp. 859-864, (2008).

McGoveran, et al., "Long-Term Chondrocyte Viability in a Fresh Osteochondral Allograft", The Journal of Knee Surgery, vol. 15, No. 2, pp. 97-100, (2002).

Muldrew, et al., "Localization of Freezing Injury in Articular Cartilage", Cryobiology, vol. 31, pp. 31-38, (1994).

Muldrew, "Cryopreservation of Articular Cartilage", Abstracts, 33rd Annual Meeting of the Society for Cryobiology, pp. 616-617, No. 6, Indianapolis, Indiana, Aug. 21, 1996.

Muldrew, et al., "Cryobiology of Articular Cartilage: Ice Morphology and Recovery of Chondrocytes", Cryobiology, vol. 40, pp. 102-109, (2000).

Muldrew, et al., "Transplantation of Articular Cartilage Following a Step-Cooling Cryopreservation Protocol", Cryobiology, vol. 43, pp. 260-267, (2001.

Muldrew, et al., "Chondrocyte Sensitivity to Lethal Injury Correlates with Proximity to the Cartilage Surface", Abstracts, 32nd Annual Meeting of the Orthopaedic Research Society, pp. 589, No. 136, New Orleans, Louisiana, Feb. 1986.

Pegg, et al., "Fractures in Cryopreserved Elastic Arteries", Cryobiology, vol. 34, pp. 183-192, (1997).

Rzepakovsky, "The Effect of Long Term Storage at -80° C on the Cell Viabillity in Cartilage Tissue", Study Report, No. LAB-0161, 3 pages, (2005).

Rzepakovsky, "The Effect of Long Term Storage in Liquid Nitrogen on the Cell Viabillity in Cartilage Tissue", Study Report, No. LAB-0161, 3 pages, (2006).

Satpathy, et al., "Loading red blood cells with trehalose: a step towards biostabilization", Cryobiology, vol. 49, pp. 123-136, (2004).

Schachar, et al., "Transplantation of Cryopreserved Osteochondral Dowel Allografts for Repair of Focal Articular Defects in an Ovine Model", The Journal of Bone and Joint Surgery, Inc., vol. 17, pp. 909-920, (1999).

Dimethyl sulfoxide, SIGMA Product Information, 2 pages, Dec. 2003.

Suganuma, et al., "Green tea and cancer chemoprevention", Mutation Research, vol. 428, pp. 339-344, (1999).

Teng, et al., "Enhancing Osteochondral Allograft Viability", Clin Orthop Relat Res, vol. 466, pp. 1804-1809, (2008).

Towns, "Moisture content in proteins: its effects and measurement", Journal of Chromatography A, vol. 705, pp. 115-127, (1995).

Van Steensel, et al., "Optimization of cryopreservative procedures for human articular cartilage chondrocytes", Arch Orthop Trauma Surg, vol. 113, pp. 318-321, (1994).

Williams, et al., "Prolonged Storage Effects on the Articular Cartilage of Fresh Human Osteochondral Allografts", J Bone Joint Surg Am, vol. 85, pp. 2111-2120, (2003).

Williams, et al., "Analysis of Cartilage Tissue on a Cellular Level in Fresh Osteochondral Allograft Retrievals", Am J Sports Med, vol. 35, No. 12, pp. 2022-2032, (2007).

XP-002337043: Derwent, "Preservation solution for cells and tissues contains polyphenol as effective component", 1 page, (2002).

XP-002337044: Derwent, "Composition for preservative of animal cell, organs such as skin, blood vessel, cornea, kidney, heart, liver, lungs, placenta or pancreas, contains preset amount of epigallocatechin gallate as active ingredient", 1 page, (2003).

Zoberi, et al., "Radiosensitizing and anti-proliferative effects of resveratrol in two human cervical tumor cell lines", Cancer Letters, vol. 175, pp. 165-173, (2002).

* cited by examiner

METHOD AND APPARATUS FOR FREEZING OR THAWING OF A BIOLOGICAL MATERIAL

FIELD OF THE INVENTION

This invention relates to a method and an apparatus for freezing or thawing of a biological material.

LIST OF REFERENCES

The following references are considered to be pertinent for the purpose of understanding the background of the present invention:
1. U.S. Pat. No. 5,873,254;
2. WO 03/056919;
3. WO 03/020874;
4. U.S. Pat. No. 6,337,205 (Wisniewski);
5. U.S. Pat. No. 5,863,715 (Rajotte).

BACKGROUND OF THE INVENTION

In freezing of biological material, two freezing stages are recognized: nucleation and crystallization. In the first stage ice nucleation occurs in the solution outside the cells. In order to minimize cellular damage, it is critical to control during this stage (nucleation) both the interface velocity of the cold front and the direction of thermal gradient within the object. Normally, in some biological materials (e.g. blood, cell suspensions, plasma, semen and other liquid samples) the best survival is obtained when the freezing rate at this stage is relatively rapid (10° C./min or more). In other cases (e.g. organs or organ fragments), it is accepted that a slow freezing rate at this stage (0.5° C./min or less) would improve freezing.

The next stage is that of crystallization, an exothermic process that produces latent heat within the frozen material, causing a period of time when the biological material remains isothermal, or even experiences an increase in temperature: latent heat exudes from the biological material and thus, although the material is being cooled no temperature change is observed or the temperature may even rise. This in turn causes spontaneous freezing and thawing cycles which are hazardous to the biological material.

Permitting osmosis of water out of the cells at this stage would reduce damage to the cells, and the increase of intracellular concentration would cause the cells to vitrify rather than freeze. This is affected by the rate of freezing, and thus, in order to optimize the biological material's survival of this stage control of the rate of freezing is important. The optimal rate depends on the type and composition of the biological material being frozen.

In addition to the above, cryopreservation of material having a large volume (e.g. tissues, organs or portions thereof) is associated with heat transfer and mass problems that are not associated to the same extent with cryopreservation of isolated cells. For example, in conventional freezing methods, ice grows at an uncontrolled velocity and morphology and may disrupt and kill cells by mechanical destruction of the tissue architecture. Due to the large size of macroscopic material, large uncontrolled thermal gradients may develop from the surface of the sample to its interior.

One method that was devised to allow freezing biological material of a large volume is disclosed in U.S. Pat. No. 5,863,715. In this patent, the biological material is placed in a flexible container, such as a bag. The bag is then flattened in a holder that maintains an essentially constant cross-sectional area of the bag in order to minimize thermogradients. The holder is then cooled along with the bag contained therein.

It is well established that directional freezing, a process in which a cold front propagates in a controlled manner through the frozen object, improves the chances of biological material to survive freezing and thawing. In this process a temperature pattern (or gradient) is established in the object being frozen to form a propagation cold front within the object, resulting in improved chances of survival.

A successful method of directional freezing is disclosed in U.S. Pat. No. 5,873,254. In this patent, a freezing apparatus is used to establish a laterally varying thermal gradient and the biological sample is moved along the thermal gradient at a controlled velocity. Additional methods were developed in order to improve the freezing of large volume objects. For example, WO 03/056919 discloses freezing biological samples via an isothermal stage, wherein the temperature is changed until temperature of the sample in an outer zone equals intermediate temperature and changing temperature until the majority of the sample is in a final temperature. This method may be used in conjunction with directional freezing but is not limited thereto. Another process is disclosed in WO 03/020874 in which the biological sample is agitated during its migration along a thermal gradient.

A method for cryopreservation of a biopharmaceutical is disclosed in U.S. Pat. No. 6,337,205. The sample to be frozen is inserted into special oblong vials that have special appendages, termed "ice crystal-nucleating structures", situated at the opposite ends of the vial's oblong cross-section. The vials are placed within a compartment of a cryopreservation apparatus, said compartment containing a cryopreservation fluid. A freezing front is then generated at one of the walls of the apparatus that is adjacent to one of the appendages, and propagates through the cryopreservation fluid. Due to the special shape of the appendage, nucleation begins at the appendage, and thus the cold front propagates within the sample in a direction that is away from the cooling wall and along the oblong cross section of the vial. In an alternative disclosed in U.S. Pat. No. 6,337,205, two cold fronts may be generated in the compartment, in opposing directions, by opposing walls of the apparatus. In this method, the freezing of the sample is achieved indirectly, in the sense that the cooling wall of the apparatus cools the cryopreservation fluid, which in turn cools the vial (and the sample within it).

SUMMARY OF THE INVENTION

The present invention is based on the realization that freezing and/or thawing of a biological material, for example an organ to be preserved for subsequent transplantation, may be carried out with minimal damage by placing the biological material in tight contact with at least one, preferably between at least two heat exchangers, and controlling the temperature so as to yield a gradual temperature change in the biological material that will give rise to directional freezing. More particularly, this is achieved by one or more controlled thermal gradients within the material, inflicted by the heat exchangers, such that a freezing temperature front propagates within the material, so as to gradually freeze the entire material in a directional manner.

According to a first aspect of the invention there is provided a method for changing the temperature of a biological material from a first temperature to a second temperature within a time period, one of the said first or second temperatures being above freezing temperature and the other being below freezing temperature, comprising: placing the biological material tightly in contact with at least one, preferably in tight contact between at least two, heat exchangers and inducing a heat exchange scheme comprising controlling the temperature in at least one of said heat exchangers such that a freezing temperature front propagates in said material away from said heat exchangers According to another aspect there is provided an apparatus for changing the temperature of a biological material from a first temperature to a second temperature, one of the said first or second temperature being above freezing temperature and the other being below freezing temperature, the apparatus comprising: a heat exchange unit comprising at least one heat exchanger for placement in contact with the biological material, one or more of the at least one heat exchanger being equipped with a temperature control arrangement including one or both of a heating and a cooling arrangement, at least one of said heat exchangers being equipped with a cooling arrangement; and a control unit for inducing a temperature changing operational sequence comprising controlling temperature of at one or more of the least one heat exchanger such as to yield a freezing temperature front that propagates within said material away from at least one of said heat exchangers, whereby temperature of the material changes from said first to said second temperature.

At times the heat exchange unit comprises at least two heat exchangers situated opposite one another with a space therebetween for accommodating the biological material, each of said heat exchangers being equipped with one or both of a heating and a cooling arrangement, at least one of said heat exchangers being equipped with a cooling arrangement Said controlling typically involves gradually changing the temperature of at least one, typically more than one, of the heat exchangers.

As will be appreciated, during operation, preferably one but usually more than one heat exchangers will have a temperature below freezing in at least part of the temperature changing operational sequence. Additionally, while in some embodiments of the invention the heat exchangers may have an essentially constant temperature throughout the temperature changing operational sequence, in other embodiments of the invention the temperature of one or more of the heat exchangers may be changed, e.g. gradually, during the temperature changing operational sequence.

While changing of the temperature of the biological material, in accordance with the invention, a temperature gradient is formed within the biological material. This requires that during operation at least one of the heat exchangers will have a temperature below freezing point. Consequently, a portion of the biological material adjacent such heat exchanger freezes first. The interface between a frozen portion and a non frozen portion in the biological material creates a "freezing temperature front", which may then gradually propagate in said material as other portions of the material gradually freeze. The rate of propagation may be controlled by the temperature differential between heat exchangers and also by a change in temperature in one or both of the heat exchangers, or by changing the distance between the two heat exchangers. It should be noted that a freezing temperature front also occurs while thawing during gradual transition of the biological material from frozen to a thawed state, and such front also propagates in the material in a similar manner to that described above. Similarly, during thawing, the rate of propagation of the freezing temperature front may be controlled by a change in the temperature of one or both of the heat exchangers.

In accordance with one embodiment of the invention a temperature differential between the two heat exchangers is maintained at least during part of the temperature change period, such that the freezing temperature front propagates from one side, adjacent one of the heat exchangers, to the other side of the biological material adjacent the other heat exchanger.

In accordance with another embodiment, the temperature of both heat exchangers is maintained at essentially the same temperature such that freezing temperature front propagates from the periphery of the biological material, adjacent said heat exchangers, towards the interior of the material, somewhat in between the two heat exchangers. While in the former embodiment, the freezing will be in one direction throughout the entire biological material, in the latter embodiment the freezing will in fact be bi-directional.

In accordance with an embodiment of the invention a plurality of heat exchangers are provided for contacting the biological material from a plurality of directions. Thus, in accordance with this embodiment, a heat exchange scheme may be induced, with a plurality of freezing temperature front propagate within the biological material towards its interior. In a specific embodiment a plurality of heat exchangers for essentially surrounding the biological material are provided. In the latter embodiment, a heat exchange scheme in which a freezing temperature front propagates to the biological material's interior from all peripheral portions thereof. This will give rise to multidirectional freezing from the periphery towards the material's interior.

As may be appreciated, at times the at least two heat exchangers are not independent bodies but rather may be part of one heat exchange device. For example, in one embodiment the at least two heat exchangers may be integrally formed with a main body that holds the temperature control arrangement.

By another exemplary embodiment, the heat exchangers are formed as a tubular body, which may have a cylindrical, elliptical, oval, polygonal or any other suitable cross-sectional shape. Such a tubular heat exchange body is adapted to encase the biological material during temperature change according to the invention.

A plurality of heat exchangers may be so configured such that when brought together they define a tubular heat exchange structure. By a non-limiting example, two heat exchangers that are trough-shaped, when brought together form a tubular heat exchange structure. Additional heat exchangers may be provided in for insertion into the open ends of the tubular structure, to ensure tight engagement of the biological material with the heat exchangers. Such additional heat exchangers may be provided also in the case of the "another exemplary embodiment" described above.

In accordance with one embodiment of the invention more than one, and preferably all of the heat exchangers comprise or are associated with a cooling arrangement for cooling the internal, biological material-facing surface thereof.

In accordance with another embodiment, at least one, and preferably all of the heat exchangers comprise or are associated with a heating arrangement for heating the internal, biological material-facing surface thereof.

The harvested organ may typically be first cooled from a harvested temperature, typically about 37° C. to a lower temperature, still above freezing, e.g. a temperature within the range of 2-6° C. This may be carried by routine refrigeration methods. Thereafter such harvested biological material may be further cooled, by the method and/or apparatus of the invention to a lower temperature, e.g. about −20° C. to −80° C., at times to, a temperature in the range of −30° C. to −70° C., and typically at a temperature within the range of −40° C. to −60° C. Thereafter the frozen biological material may be further cooled, e.g. by the use of liquid nitrogen to a temperature of about −196° C. and stored at that temperature.

Thawing of a biological material frozen in accordance with the invention may be achieved by conventional means or may also be carried out in accordance with the teaching of the invention. This thawing method may be applied to frozen biological material that was not frozen by the method of the present invention. Typically, the temperature is first gradually increased to a temperature still below freezing and then the biological material is further warmed to a temperature of a few degrees above freezing, which may be carried out in accordance with the teaching of the present invention.

In some embodiments of the invention, particularly in case of the need to change the temperature of a biological material which has non homogenous thermal properties, e.g. and organ with different tissue types, it may be desired to control the temperature of the heat exchanger so as to have somewhat different temperatures at different zones of the heat exchanger that are in contact with different portions of the biological material, e.g. different portions of the harvested organ intended for preservation. Thus, heat exchangers may be equipped, in accordance with some embodiments of the invention, with two or more independent cooling and/or heating arrangements at different regions of the heat exchanger to yield different temperatures at different regions thereof.

Many options are known in the art that enable imposing a different temperature regime on a single heat exchanger. This includes constructing the heat exchanger from distinct blocks, each having a separate temperature control (and optionally each having a sensor) and separate coolers and/or heaters. Alternatively a single heating or cooling unit may be configured to generate a predefined temperature gradient by forcing the cooling fluid to flow from one side to the other (instead of bi-directional flow), causing a gradient which would be dependent on the geometry of the cooling block and of the cooling conduits. For example, a cooling fluid conduit may be configured such that it would be relatively far from the biological material facing surface when entering a heat exchanger, and grow closer to the biological material facing surface until exiting the heat exchanger at a place near the biological material facing surface. Yet another option is using several heaters or coolers, each controlled separately such that different temperatures would be imposed in different locations in a single block.

In accordance with one embodiment of the invention, the cooling arrangement includes conduits for cooling fluids, which conduits are associated with or are formed within the heat exchangers. Such conduits are in flow communication with a cooling fluid reservoir, typically through flow control valving means. The heating arrangement may also involve such conduits, which may be the same or different than the conduits used for the cooling fluid. By controlling the rate of flow and/or the temperature of the fluid that enters the conduits, the temperature of the heat exchangers may be controlled. The cooling fluid is typically liquid nitrogen. An example of a heating fluid is water or alcohol.

In accordance with another embodiment, the heating arrangement includes electric heating modules.

The heat exchange unit is typically insulated from the environment, so as to minimize heat loss and improve heat transfer to or from the biological material. The insulating material may comprise Styrofoam, glass wool, cellulose wool, ceramic foams, polyethylene, vacuum, and generally in any type of insulation known per se.

In order to improve conduction of heat to or from the biological material, particularly in case of an organ of an irregular shape, at least one of the heat exchangers may be displaceable to yield a better contact between the heat exchangers and the biological material or ensure relatively tight fitting of the biological material into the space formed between the two opposing heat exchangers.

It should be noted, that the two opposing heat exchangers may, under some embodiments, be kept always parallel to one another. However, it is clear that under other embodiments, at least one of the heat exchangers may be tilted to ensure better contact with the biological material, whereby during operation the two heat exchangers will not be parallel to one another.

In accordance with other embodiments of the invention, the heat exchangers may have an irregular shape, for example, so as to fit the external contours of the biological material, e.g. the external contours of a heart, a kidney, etc. Also, in accordance with embodiments of the invention, there may be more than two heat exchangers, two or more on one side of the biological material and two or more on the other. Both these embodiments constitute different ways for achieving good contact between the heat exchangers and the biological material, particularly such having an irregular shape (e.g. a harvested organ), thereby ensuring efficient temperature exchange with the biological materials.

At times, use may be made with heat conducting fitting members that are placed between a heat exchanger and the organ and serve as a bridge for conducting heat or cold between the heat exchanger and the surface of the biological material.

At times, particularly for the purpose of ensuring sterility, the biological material may be included within a chamber or a bag. In case the container is a rigid container (e.g. a vial), it may example, be inserted into a liquid that transfers the heat or cold from the heat exchanger to the container (and then from the vial to the container to the biological material, directly or through a small amount of a cryopreservation solution). Preferably, the container is held in tight contact with at least one or two heat exchangers, which contact is direct contact, such that heat is conducted from (or to) the heat exchanger directly to (or from) the wall of the container (with the possible exception of a thin film such as liquid nitrogen vapor).

The apparatus may comprise one or more temperature sensors for sensing the temperature of the heat exchangers or that of the biological material.

The control unit may comprise a dedicated computer or external desktop or laptop computer or PLC (Programmable Logic Controller). It may also comprise a user interface allowing a user to control or override the pre-set temperature regime.

In addition, in some cases it may be desirable to provide additional information to the control unit (information such as freezing temperature front propagation feedback). This information may be used for example as feedback for control of operation and also for quality assurance of the resultant temperature change of the biological material. The sensor reading may also allow the control unit and/or user to adapt the temperature regime to the actual changes within the biological material. Finally, the data so collected may be stored in any form (such as digital data or printed documentation) for any use, including research and development.

Thus, in addition to temperature sensors the system might include additional sensors such as:

1. One or more CCD cameras that may be used for observation of the biological material and crystals formed therein;

2. One or more temperature sensors (e.g. a thermocouple or infrared camera or detector) at one or more locations within the biological material, that may be used to record the temperature pattern at any time and the changes in temperature during operation;

3. One or more electrical resistance (impedance) measuring units that allow detection of changes within the biological material during operation.

Finally, ultrasound may also be used to follow the freezing temperature front propagation inside the biological material. In such case an ultrasound transmitter may be used, for example within the chamber, and the propagation of the interface (cold front) may be monitored by ultrasound readings as known in the art.

BRIEF DESCRIPTION OF THE DRAWINGS

In order to understand the invention and to see how it may be carried out in practice, embodiments will now be described, by way of non-limiting example only, with reference to the accompanying drawing, in which.

DETAILED DESCRIPTION OF THE INVENTION

Figure 1:
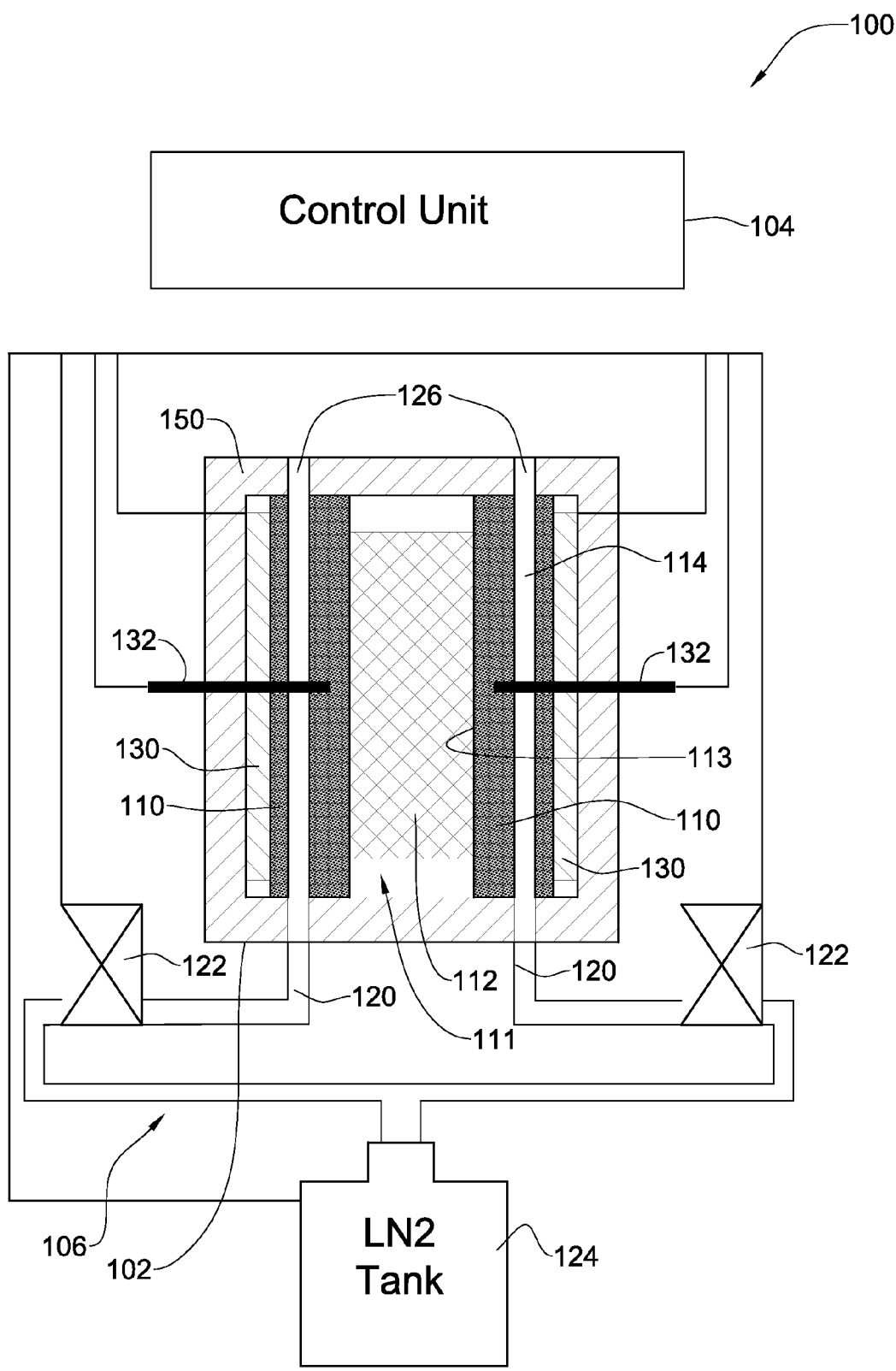
FIG. 1 is a schematic cross sectional view of a apparatus according to one embodiment of the invention.

The apparatus and method of the present invention are for changing the temperature of a biological material past a freezing point for either freezing a biological material, particularly a harvested organ intended for subsequent transplantation, or for thawing a biological material, e.g. for subsequent transplantation of a preserved organ in an organ recipient. The controlled freezing in accordance with the invention gives rise to a control, directional ice crystal generation in the organ.

Reference is first being made to FIG. 1 which is a schematic representation of an apparatus in accordance with the invention generally designated 100. The main components of the apparatus include a heat exchange unit generally designated 102, a control unit 104 and a cooling liquid supply system generally designated 106.

A heat exchange unit 102 includes, in this specific embodiment, two heat exchangers 110 defining a space 111 between them for accommodating the biological material 112 to be frozen or thawed, which is typically a harvested organ or liquid biological sample (such as blood or semen) intended for cryopreservation for subsequent use for in vitro purposes or in transplanting in an organ recipient. The heat exchangers are typically made of material with high thermal conductivity, e.g. a metal such as brass, gold, gold plated brass, and others. Occasionally the surface of the heat exchanger may be coated by a thin layer made of polymeric material, glass, etc.

In the apparatus schematically illustrated in FIG. 1, two opposing heat exchangers are included. However, as already pointed out above, it is possible also for the apparatus to have three or more heat exchangers to permit the achievement of complex heat exchange patterns, for improved heat exchange contact with irregularly shaped biological materials, etc. Furthermore, according to some embodiments of the invention, the heat exchangers are displaceable to ensure relatively tight attachment to the biological material (e.g. to tilt at least one of them thus changing the shape of space 111 or move at least one of them thus changing the size of space 111).

Heat exchangers 110 may be positioned horizontally, vertically, or in any other suitable alignment. They may have an essentially flat internal, material facing surface 113 or may have an irregular shape, e.g. concave or convex, to permit better association with external contours of the biological material to be frozen or thawed by the apparatus.

For cooling, heat exchangers 110 are provided with conduits 114 that are linked to cooling system 106 through tubings 120. Cooling system 106 comprises flow control valves 122, disposed within tubings 120 and a cooling fluid reservoir 124, with the cooling fluid being typically liquid nitrogen, although other cryogenic fluids may also of course be used.

Illustrated herein is a single conduit 114 in each of heat exchangers 110 although as may be appreciated, the heat exchanger may be equipped with more than one conduit. Also, independent valves may be provided for different conduits, for example, for achieving different temperature at different regions of the heat exchanger.

In accordance with one embodiment, spent cooling fluid is discharged to the atmosphere through an exhaust 126. Alternatively, it is also possible to have a recycling arrangement whereby spent fluid is cooled again and returned back to reservoir 124.

A heat exchange unit further includes electrical heating modules 130 which are in tight association with the heat exchangers. Thus, heat exchangers may be either heated or cooled or through a combination of cooling and heating, a fine temperature control may be achieved.

The heat exchange unit is typically insulated by means of insulator 150.

The apparatus also comprises temperature sensors 132, linked to controlled unit 104. Two temperature sensors are shown in this schematic illustration, although it may be appreciated that more temperature sensors may be included, e.g. different sensors at different zones of the heat exchangers, sensors for sensing the temperature of the biological material, etc. Control unit 104 is also linked to electric heating elements 130, valves 122 and cooling reservoir 124.

Operation of an Apparatus

In operation the temperature the heat exchangers 110 is changed to an initial temperature. At that time a biological material 112 is placed within the apparatus such that the biological material (or the container holding the biological material) is held tightly by the heat exchangers. This may be achieved for example by moving at least one of the heat exchanger closer to the other, with the biological material sandwiched between them, but taking care not to damage the biological material. Preferably the biological material is placed in the apparatus at a predetermined initial temperature, which may be different from that of the heat exchangers of the apparatus. Once the biological material is in place, the temperature of at least one of the heat exchangers of the apparatus is changed for a period of time. As detailed below, the pattern and rate of temperature change may be preset or may be modified during operation in response to processes in the biological material.

It is well established that different biological samples require different freezing protocols in order to survive freezing and thawing and remain biologically active. Many such protocols are known in the art. Examples for such protocols are given in U.S. Pat. No. 5,873,254. For example: freezing of semen may begin at a slow rate (e.g. 1° C./minute) from a temperature of 30° C. to 4° C. Next, a faster rate (30° C./minute) would be used until the semen reaches about −50° C., when crystallization ceases. To achieve this protocol, the apparatus may be set such that a sensor within the biological material (in this example semen) would dictate the changing of rate of temperature change or a CCD camera or ultrasound transmitter would be used to detect the time when a change of rate is desired (e.g. after lipid phase transition or crystallization are complete) and then change the heat exchanger temperature regime, either automatically or by a user.

The rate of temperature change in the biological material would be proportional to the temperature difference between the material and the heat exchangers, the rate of change in the heat exchangers' temperature and the thermal properties of the biological material. Thus the heat exchangers' temperature regime may be set according to calculations based on the above parameters, or according to trial and error experimentation, or on both.

The time upon which a change in the temperature regime of any heat exchanger (or portion of a heat exchanger) would be affected may be set according to any calculable or observable parameter. Accordingly the control unit may be configured to change the heat exchangers' temperatures upon reaching of certain time or temperature thresholds. Some non-limiting examples are:

(a) A time-dependent change, namely a change that occurs within a given time after operation began;

(b) A temperature-dependent change that begins at a time when the heat exchanger's or the biological material's measured temperature reaches a specific temperature or is within a pre-defined temperature range; or (c) A temperature profile-dependent sequence that is initiated at time when a certain temperature gradient is achieved within the biological material.

Alternatively, the change of temperature regime may be in accordance with a process observed within the biological material, such as upon the beginning or termination of any one of the following processes: seeding, lipid phase transition, nucleation, crystallization, glass transition. The change of a regime may be effected automatically by the controller through feedback from one or more sensors of any kind. Alternatively this change of regime may be manipulated manually by the user in real time in accordance with said sensor readings.

Finally, as noted above, the temperature regime of each of the heat exchangers may be different from that of the other, and the temperature difference between them may change during operation. This difference may also be preset, but may also be changed during operation, according to the sensor feedback from the heat exchangers or the biological material or according to any of the abovementioned processes that are observed within the biological material.

It is appreciated that the above discussion regarding operation of an apparatus according to a specific, non-limiting embodiment of the present invention, applies, mutatis mutandis, also to the method of the invention, even when an apparatus according to the invention is not used.

Those skilled in the art will readily appreciate that various modifications and changes can be applied to the embodiments of the invention as hereinbefore exemplified without departing from its scope defined in and by the appended claims.

The invention claimed is:

1. A method for changing the temperature of a biological material from a first temperature to a second temperature within a time period, one of the said first or second temperatures being above freezing temperature and the other being below freezing temperature, comprising:

providing an apparatus comprising an insulator having inner and outer walls and at least two opposing heat exchangers, each heat exchanger having a first end and a second end, the heat exchangers being spaced from each other along their entire longitudinal dimension by a space, and each heat exchanger comprising a fluid conduit extending along the entire longitudinal dimension thereof between an inlet tube and an outlet tube spaced by the longitudinal dimension, the inlet and the outlet tubes projecting from the first and second ends of the heat exchangers towards the inner walls of the insulator;

placing the biological material or a container holding the biological material in the space between the at least two opposing heat exchangers such that the biological material or the container holding the biological material is tightly in contact with each of the two opposing heat exchangers along a majority of the longitudinal dimension, and controlling the temperature in one or more of the at least two heat exchangers by means of the fluid conduits such that a freezing temperature front propagates in the material away from the one or more heat exchangers.

2. The method of claim 1, wherein controlling comprises gradually changing the temperature of at least one of the heat exchangers.

3. The method of claim 1, for freezing the biological material.

4. The method of claim 1, wherein the biological material is an organ for transplantation.

5. The method of claim 1, wherein there is a temperature difference between the at least two opposing heat exchangers in at least one stage during the time period.

6. The method of claim 5, wherein the freezing temperature front propagates within the biological material in a direction from one heat exchanger to the other.

7. The method of claim 1, wherein the temperature of the at least two opposing heat exchangers is essentially the same and the freezing temperature front propagates from zones of the biological material adjacent the two heat exchangers to the biological material's interior.

8. The method of claim 1, wherein the at least two opposing heat exchangers essentially surround the biological material.

9. The method of claim 1, wherein controlling the temperature in one or more of the at least two heat exchangers is performed by means of a cooling arrangement comprising one or more cooling fluid conduits extending along the longitudinal dimension.

10. The method of claim 9, wherein rate of flow of cooling fluid in the one or more cooling fluid conduits is controlled by flow control valves.

11. The method of claim 1, wherein the two heat exchangers are disposed within the insulator, the inner walls being opposite walls and the conduits extending between the opposite walls.

12. The method of claim 1, wherein the inner side walls of the heat exchanger are in direct contact with sides of the biological material or the container holding the biological material.

13. An apparatus for changing the temperature of a biological material from a first temperature to a second temperature, one of the first or second temperatures being above freezing temperature and the other being below freezing temperature, the apparatus comprising:

a heat exchange unit comprising an insulator having inner and outer walls and at least two heat exchangers, each heat exchanger having a first end and a second end, the heat exchangers being spaced being spaced apart from each other along their entire longitudinal dimension by a space, and configured for placing the biological material or a container holding the biological material in the space in tight contact with the heat exchangers along a majority of the longitudinal dimension, one or more of the at least two heat exchangers being equipped with one or both of a heating and a cooling arrangement, and each heat exchanger comprising a fluid conduit extending along the entire longitudinal dimension thereof between and inlet tube and an outlet tube spaced by the longitudinal dimension, the inlet and the outlet tubes projecting from the first and second end of the heat exchangers towards the inner walls of the insulator, at least two of the heat exchangers being equipped with a cooling arrangement for cooling the internal, biological material facing surface of the heat exchanger; and a control unit for inducing a temperature changing operational sequence comprising controlling the temperature of one or more of the at least two heat exchangers by means of the fluid conduits such as to yield a freezing temperature front that propagates within the material away from at least one of the heat exchangers, whereby temperature of the material changes from the first to the second temperature.

14. The apparatus of claim 13, wherein the controlling comprises gradually changing the temperature of one or more of the at least two heat exchangers.

15. The apparatus of claim 13, wherein one or more of the at least two heat exchangers comprise a heating arrangement for heating the internal, biological material facing surface of the heat exchangers.

16. The apparatus of claim 13, wherein the cooling arrangement comprises one or more cooling fluid conduits in flow communication with a cooling fluid reservoir.

17. The apparatus of claim 15, wherein the heating arrangement comprises an electric heating module.

18. The apparatus of claim 13, wherein the heat exchange unit is thermally insulated.

19. The apparatus of claim 13, comprising at least one or more temperature sensors for monitoring temperature of one or more of the at least two heat exchangers and the biological material.

20. The apparatus of claim 13, wherein during at least some of the operational sequence there is a temperature difference between the two heat exchangers.

21. The apparatus of claim 13, wherein the two heat exchangers are displaceable.

22. The apparatus of claim 13, wherein the control unit is adapted to control the temperature of each of the two heat exchangers independently.

23. The apparatus of claim 16, wherein the one or more cooling fluid conduits extend along the longitudinal dimension.

24. The apparatus of claim 23, wherein rate of flow of cooling fluid in the one or more cooling fluid conduits is controlled by flow control valves.

25. The apparatus of claim 13, wherein the two heat exchangers are disposed within the insulator, the inner walls being opposite walls and the conduits extending between the opposite walls.

26. The method of claim 13, wherein the inner side walls of the heat exchanger are in direct contact with sides of the biological material or the container holding the biological material.

27. A method for changing the temperature of a biological material from a first temperature to a second temperature within a time period, one of the said first or second temperatures being above freezing temperature and the other being below freezing temperature, comprising:

providing an insulator having inner and outer walls and at least two heat exchangers each having a first end and a second end, the heat exchangers having opposing material facing surfaces spaced from each other along their entire longitudinal dimension by a material receiving space, and each heat exchanger comprising a fluid conduit extending along the entire longitudinal dimension thereof between and inlet tube and an outlet tube spaced by the longitudinal dimension, the inlet and outlet tubes projecting from the first and second ends of the heat exchangers toward the inner walls of the insulator;

placing the biological material or a container holding the biological material in the space in tight contact with each of the surfaces, and controlling the temperature in one or more of the at least two heat exchangers by means of the fluid conduits such that a freezing temperature front propagates in the material away from at least one of the heat exchangers.

28. The method of claim 27, wherein rate of flow of cooling fluid in the one or more cooling fluid conduits is controlled by flow control valves.

29. The method of claim 27, wherein the two heat exchangers are disposed within the insulator, the inner walls being opposite walls and the conduits extending between the opposite walls.

30. An apparatus for changing the temperature of a biological material from a first temperature to a second temperature, one of the first or second temperatures being above freezing temperature and the other being below freezing temperature, the apparatus comprising:

a heat exchange unit comprising an insulator having inner and outer walls and at least two heat exchangers each having a first end and a second end, the heat exchanger having opposing material facing surfaces spaced from each other along their entire longitudinal dimension by the biological material or a container holding the biological material receiving space, wherein the material receiving space is configured for placement therein of the biological material in tight contact with the material facing surfaces along the majority of the longitudinal dimension, and wherein one or more of the at least two heat exchangers being equipped with one or both of a heating and a cooling arrangement, and the heat exchangers each comprising a fluid conduit extending along the entire longitudinal dimension thereof between an inlet tube and an outlet tube spaced by the longitudinal dimension, the inlet and outlet tubes projecting from the first and second ends of the heat exchangers toward the inner walls of the insulator, at least one of the heat exchangers being equipped with a cooling arrangement, the cooling arrangement comprising one or more cooling fluid conduits extending along the longitudinal dimension in flow communication with a cooling fluid reservoir; and a control unit for inducing a temperature changing operational sequence comprising controlling the temperature of one or more of the at least two heat exchangers by means of the fluid conduits such as to yield a freezing temperature front that propagates within the material away from at least one of the heat exchangers, whereby temperature of the material changes from the first to the second temperature.

31. The apparatus of claim 30, where the two heat exchangers are disposed within the insulator, the inner walls being opposite walls and the conduits extending between the opposite walls.

* * * * *